US007687243B1

(12) United States Patent
Crook

(10) Patent No.: US 7,687,243 B1
(45) Date of Patent: Mar. 30, 2010

(54) AUTOMATED METHOD FOR DETECTING APOPTOSIS IN CELLS

(76) Inventor: Tonia M. Crook, 1010 Burkhart Rd., Lexington, NC (US) 27292-0746

( * ) Notice: Subject to any disclaimer, the term of this patent is extended or adjusted under 35 U.S.C. 154(b) by 0 days.

(21) Appl. No.: 11/447,556

(22) Filed: Jun. 6, 2006

Related U.S. Application Data

(60) Provisional application No. 60/687,685, filed on Jun. 6, 2005.

(51) Int. Cl.
*G01N 33/53* (2006.01)
(52) U.S. Cl. ...................................................... 435/7.9
(58) Field of Classification Search ................. 435/7.9, 435/4, 7.1, 7.2, 283.1, 289.1, 287.3
See application file for complete search history.

(56) References Cited

U.S. PATENT DOCUMENTS

| | | | | |
|---|---|---|---|---|
| 5,776,414 | A * | 7/1998 | Itani et al. ...................... | 422/67 |
| 5,834,196 | A | 11/1998 | Reutelingsperger ............ | 435/6 |
| 5,942,396 | A * | 8/1999 | Shiff et al. ..................... | 435/6 |
| 6,004,767 | A | 12/1999 | Crouch et al. .................. | 435/8 |
| 6,586,203 | B1 * | 7/2003 | Sherr et al. ................. | 435/69.1 |
| 6,635,802 | B1 * | 10/2003 | Piedrahita et al. ............. | 800/24 |
| 7,026,472 | B2 * | 4/2006 | Dou et al. .................... | 540/355 |
| 2002/0037832 | A1 * | 3/2002 | Nielsen et al. .................. | 514/2 |
| 2003/0017462 | A1 | 1/2003 | Hewitt ........................... | 435/6 |
| 2003/0152555 | A1 * | 8/2003 | Liu et al. .................... | 424/93.7 |
| 2005/0032204 | A1 * | 2/2005 | Rodgers et al. .......... | 435/288.5 |
| 2005/0244812 | A1 | 11/2005 | Ziv et al. ........................ | 435/4 |
| 2006/0019333 | A1 * | 1/2006 | Rodgers et al. ............... | 435/41 |
| 2006/0046298 | A1 | 3/2006 | Key et al. ...................... | 436/43 |
| 2006/0111423 | A1 * | 5/2006 | Zeligs ........................ | 514/410 |
| 2006/0205710 | A1 * | 9/2006 | Schlienger ............. | 514/211.04 |
| 2007/0129306 | A1 * | 6/2007 | Szeto et al. ................... | 514/13 |
| 2007/0160496 | A1 * | 7/2007 | Thelu .......................... | 422/63 |

OTHER PUBLICATIONS

Identification of Programmed Cell Death in Situ via Specific Labeling of Nuclear DNA Fragmentation; Gavvrieli, et al., The Journal of Cell Biology, vol. 119, No. 3, pp. 493-501 Nov. 1992.
False positive staining in the TUNEL assay to detect apoptosis in liver and intestine is cause by endogenous nucleases and inhibited by diethyl pyrocarbonate; Strhelin, et al., Dept. of Clinical Pharmacology, University of Berne, Switzerland 1998.
Apoptosis and Necrosis After Reversible Focal Ischemia: An In Situ DNA; Journal of Cerebral Blood Flow & Metabolism 1996; retrieved from the internet.
Chemicon International; ApopTag Peroxidase In Situ, Apoptosis Detection Kit S7100, p. 1-36, Jan. 2005.
Aytinated TUNEL Assay; Bostick et al., undated, possible prior art.
Basic Immunochemistry; T Boenisch, undated, possible prior art.
BD Biosciences; informtion from the internet; copyright 2006.
Applied Biosystems; information from the internet; coyright 2007.
EMD Calbiochem; information from the internet; copyright 2007.
Chemicon Cell Biology; information from the internet, copyright 1994-2007.
Clontech ApoAlert Apoptosis Products Overview; informtaion from the internet; copyright 2007.
eBioscience; information from the internet; copyright 2000-2007.
MBL International Corporation; information from the internet; copyright 2002.
Partec Flow Cytometry; information from the internet; copyright 2006.
Molecular Probes; information from the internet; copyright 1996-2006.
Phoenix Flow; information from the internet; undated, possible prior art.
Caspase Assays; information from the internet; copyright 2007.
R&D Systems Molecular Group; information from the internet; copyright 2005.
Roche Applied Science Apoptosis, Cell Death and Cell Proliferation, 3$^{rd}$ Edition (174 pgs) undated, possible prior art.
Sigma-Aldrich; information from the internet; copyright 2007.

* cited by examiner

*Primary Examiner*—Ann Y Lam
(74) *Attorney, Agent, or Firm*—MacCord Mason PLLC

(57) ABSTRACT

A TUNEL assay method is claimed and described. The method comprises loading slides having mounted tissue samples into a primary stainer and testing tissue samples for apoptosis using a stainer. In one embodiment, the method includes using a stainer having a plurality of reservoirs. A reagent reservoir is loaded with anti-conjugate antibody reporter. A slide tray of the stainer is loaded with a slide having a tissue sample. The stainer adds anti-conjugate antibody reporter to the sample for a duration.

51 Claims, 1 Drawing Sheet

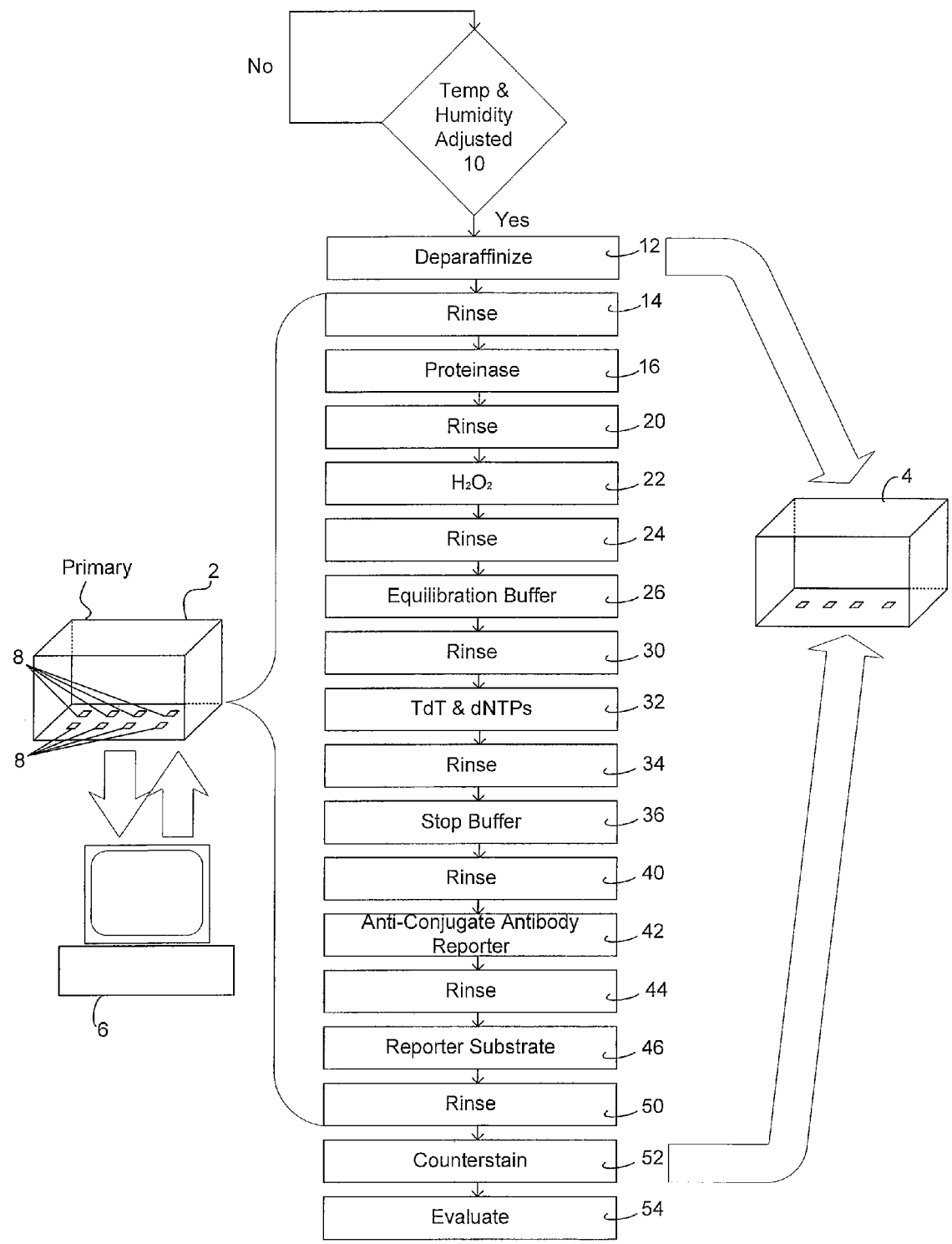

AUTOMATED METHOD FOR DETECTING APOPTOSIS IN CELLS

This application claims the benefit of U.S. Provisional Application No. 60/687,685, filed Jun. 6, 2005.

BACKGROUND

1) Field of the Invention

The present invention relates generally to diagnostic methods in histology and cytology, and more specifically to diagnostic methods for the detection of cells undergoing apoptosis.

2) Related Technology

Apoptosis is an intrinsic program of cell self-destruction inherent in eukaryotic cells. Apoptosis also plays a role in cell creation, and it is becoming increasingly apparent that the processes of cellular creation and destruction are linked by common signaling mechanisms. For example, up-regulation of one process may be accompanied by down-regulation or up-regulation of the other. Thus apoptosis may play an important role in understanding various diseases.

For example, a variety of diseases and other pathological conditions are linked to dysregulated apoptosis in a particular tissue or organ. These include, for example, general conditions related to tissue rejection, immune/inflammatory responses, ischemia and injury, cardiovascular diseases such as dilated or ischemic cardiomyopathy, myocarditis and atherosclerosis, neurodegenerative disorders such as ALS, Alzheimer's disease, Parkinson's disease and retinal degeneration, hepatic and pancreatic disorders related to viral infection or alcohol consumption, which can lead to development of insulin-dependent diabetes mellitus or infection with certain viruses, such as adenoviruses, influenzaviruses and human immunodeficiency virus.

Additionally, a variety of cell proliferative diseases and disorders are linked to dysregulated apoptosis. These include, for example, psoriasis, lupus and other autoimmune conditions such as Crohn's disease, Hashimoto's thyroiditis and arthritis, infection with certain viruses, such as human papillomavirus, Epstein-Barr virus and herpes simplex virus; as well as a variety of cancers, including mammary carcinomas, lymphomas, cervical, colon, and ovarian cancers, and neuroblastomas.

Because apoptosis plays such an important role in so many medical disorders, rapid and reproducible assays for apoptosis are of great interest to investigators in their attempts uncover disease pathways and to devise clinically relevant diagnostic and prognostic indicators of disease status in a patient.

Presently, the terminal deoxynucleotidyl transferase (TdT)-mediated biotinylated dUTP nick end labeling (TUNEL) is one method used to detect apoptosis. The TUNEL method utilizes TdT to incorporate labeled nucleotides (dNTPs) into DNA fragments containing a 3'-hydroxyl group. The label can be detected using a variety of methodologies, e.g. immunochemical or fluorescent detection. Label detection is indicative of apoptosis. While traditional TUNEL methodologies are important, they are also very labor intensive.

Traditional TUNEL methodologies require approximately four hours of constant manual attention and manipulation of samples to process 6-12 slides. Because at least two of those slides are controls, the current methodology leaves much to be desired in terms of speed, throughput, and reproducibility. The labor costs associated with these technologies are also high.

Further, while many processes are being automated in the interest of high-throughput and reproducibility, not all labs (e.g. principle investigators at small universities, small startups, or small clinical hospitals) can house, or afford the cost of, every automated system that comes out on the market.

Thus what is needed are protocols that expand the function of existing research tools. For example, many labs have stainers for histology and immunochemical purposes. The ability to use existing staining machines to perform rapid and reproducible TUNEL assays would be greatly desired.

By way of example, research laboratories perform TUNEL assays manually at great cost in skilled labor because, as noted previously, current methodologies require essentially constant attention by highly trained workers. These same labs, however, also typically have immunochemical stainers and/or histological stainers. The ability to use existing stainers to run more tests at one time, and produce more rapid and accurate test results, would significantly decrease costs to the institution and the consumer. Similar advantages and savings would also be recognized through the use of novel systems designed specifically for automating TUNEL assays.

SUMMARY

The present invention is a method of performing TUNEL assays automatically. More specifically, the present invention is a method of performing TUNEL assays using automatic stainers. The invention comprises loading slides having mounted tissue samples into a primary automated stainer and testing the tissue samples for apoptosis.

Testing comprises adding conjugate-dNTPs to tissue, adding TdT and conjugate-dNTPs, and adding anti-conjugate antibody reporter. Conjugate-dNTPs, as used herein, include any nucleotide conjugate, wherein the conjugate is capable of being bound by an antibody, and may be, for example, a protein, a carbohydrate, a steroid, etc. Anti-conjugate antibody reporters, as used herein, include any anti-conjugate antibody with any fused reporter. Preferably the conjugate-dNTPs are digoxigenin-dNTP conjugates and the anti-conjugate antibody reporter is an anti-digoxigenin antibody reporter. The reporter of the anti-digoxigenin antibody reporter is preferably a peroxidase reporter capable of reporting in the presence of a reporter substrate, which is preferably a chromogenic substrate. Reporter substrate, as used herein, is intended to include any substrate capable of being acted on by the reporter. Preferably, the interaction between the reporter and the reporter substrate produces a qualitative or quantitative effect.

In a preferred embodiment of the invention, the TUNEL assay method may comprise loading a primary automated stainer with reagents for applying to tissue samples. The reagents may include buffer, proteinase, conjugate-dNTPs, TdT, and, anti-conjugate antibody reporter. In this embodiment, if samples are paraffinized, deparaffinizing can be performed in the primary stainer or in a secondary stainer.

Using the primary stainer, Proteinase K, conjugate-dNTPs, TdT, and anti-conjugate antibody reporter are added to the tissue sample for a duration. The method may further include using the primary stainer to add a reporter substrate and a counterstain. In other embodiments, the counterstain may be added by a secondary stainer.

In this embodiment, the invention also includes evaluating samples for reporting. Typically, evaluating is achieved by visual examination of a samples using light microscopy, but others may prefer other methods.

The method also includes, in some embodiments, adjusting the temperature and humidity of the room in which the assay is to be performed.

These and other aspects of the present invention will become apparent to those skilled in the art after a reading of the following description of the preferred embodiments.

BRIEF DESCRIPTION OF THE FIGURES

FIG. 1 shows a diagram representing one embodiment of the present invention.

DESCRIPTION OF THE PREFERRED EMBODIMENTS

FIG. 1 shows a diagram representing one embodiment of a TUNEL assay method. In this embodiment, the method comprises using primary stainer 2, which may be an immunochemical stainer, and secondary stainer 4, which may be a routine histological stainer. Preferably, primary stainer 2 is a DAKO Automated Stainer (Dako North America, Inc., 6392 Via Real Carpinteria, Calif. 93013) and secondary stainer 4 is Leica Automated Stainer (Leica Microsystems Inc. 2345 Waukegan Road, Bannockburn, Ill. 60015). Other automatic stainers may also be equally suitable, and for example, both the primary and the secondary stainers could be DAKO stainers. Applicant prefers using a primary and secondary stainer to optimize efficiency and throughput. Further, because existing automatic stainers are not designed for TUNEL assays, they may not contain enough reagent reservoirs to perform complete protocols using a single machine, or they may not contain the necessary deparaffinizing or counterstaining functions.

The invention, however, may also be achieved by using a single stainer and changing reagents during the protocol or by designing a stainer capable of holding the necessary reagents and performing the necessary steps. Still, others using other stainers may wish to perform the method of the current invention using three or more stainers, for example, using one stainer for deparaffinizing, one stainer for testing, and one stainer for counterstaining. All such variations are within the scope of the present invention.

Primary stainer 2 may be in communication with processor 6 for implementing protocol. Secondary stainer 4 may also be in communication with processor 6, or may be in communication with a separate processor (not shown) for implementing protocol.

Generally, slides 8 having mounted tissue samples are loaded into automated stainer 2. Loading may be either mechanical, e.g., by a mechanical arm, or manual, e.g., by a technician. Loading procedure may also vary slightly depending on the type of stainer used to perform the invention. All loading variations are included within the present invention.

Tissue sample, as used in the present invention, is intended to include all histological and cytological techniques used to preserve cells and tissue, and is meant to be inclusive of cells and tissues. Preferably, tissue samples are fixed and embedded in paraffin. Those skilled in the art will recognize that fixatives may include formaldehyde-based fixatives, mercuric chloride-based fixatives, acetic acid-zinc chloride, periodate-lysine-paraformaldehyde (PLP), ethanol, or acetone.

Additionally, the tissue samples of the present invention may include air-dried smears, e.g., blood smears, wet smears, or cryosections.

In some embodiments of the present invention, it is desirable to adjust temperature and humidity 10 of the room in which said assay is to be performed. Preferably, the temperature is adjusted to between about 22° C. and about 26° C., more preferably, to between about 22.2° C. and about 25.6° C., and most preferably is about 24° C. Preferably, the humidity of the room is adjusted to a range from about 80% to about 88%.

In this embodiment, deparaffinizing 12 is performed in secondary stainer 4. Deparaffinizing is performed by placing slides into secondary stainer and running a deparaffinizing protocol, which may be either supplied by the manufacturer or customized. Others may perform this step in primary stainer 2, which would be within the scope of the present invention.

After deparaffinizing 12, slides are transferred to the primary stainer 2 and go through rinse 14. Rinse 14 includes a TBS buffer rinse (Signet Laboratories 2044, one 5 L pack in 5 L $DH_2O$), and more preferably includes TBS buffer rinse with Tween 20 (Signet Laboratories 2044, one 5 L pack in 5 L $DH_2O$ plus 2.5 ml Tween 20).

Primary stainer 2 performs proteinase treatment 16. Preferably proteinase treatment 16 is a Proteinase K treatment (e.g., DAKO S0809). The duration of the treatment is in between about 20 minutes and about 70 minutes long. The duration may further vary depending on the type of tissue sample being assayed. For example, proteinase 16 duration is preferably in between about 20 minutes and about 40 minutes for mice, primate, and human samples, and is even more preferably about 30 minutes. For rat samples, proteinase 16 duration is in between about 50 and about 70 minutes, and is more preferably about 60 minutes.

Proteinase K treatment typically includes adding in between about 100 μl and about 600 μl of reagent, and more preferably about 300 μl of Proteinase K per sample. Still, others may use other reagents, for example, other reagents capable of making antigens more accessible to antibodies, may prefer other amounts. And, in some samples, proteinase treatment may not be needed. For example, with cellular smears or other preparations where the proteinase activity is not needed, proteinase treatment 16 may be avoided. All such methods are within the scope of the present invention.

Primary stainer 2 performs rinse 20. Rinse 20 includes two TBS-tween rinse and blow treatments. Blow treatments, or other air treatments, are desirable, for example, to prevent dilution of reagents with buffer washes.

Primary stainer 2 performs $H_2O_2$ treatment 22. Treatment 22 is preferably a 30% $H_2O_2$ solution. Preferably the duration of treatment 22 is in between about 2 minutes and about 7 minutes, and more preferably is about 5 minutes.

Primary stainer 2 performs rinse 24. Rinse 24 includes a single TBS-tween rinse and blow treatment.

Primary stainer 2 performs an equilibration buffer treatment 26 (e.g., APOP TAG Detection Kit S7100). Other suitable pH buffers may be satisfactory as well. Preferably, treatment 26 has a duration from about 5 minutes to about 15 minutes long, and even more preferably has a duration of about 10 minutes long.

Primary stainer 2 performs rinse 30. Rinse 30 includes two TBS-tween rinse and blow treatments.

Primary stainer 2 performs a TdT and congugate-dNTP treatment 32 (e.g., APOP TAG Detection Kit S7100). The TdT and dNTP treatment, in this embodiment, are depicted as a single block 32, because TdT and dNTPs were combined to make a mix for use in primary stainer 2. Others, however, may prefer not to combine TdT and dNTPs, or may add each reagent to samples separately. Such embodiments would also be within the scope of the present invention.

Preferably, treatment 32 has a duration from about 30 minutes to about 90 minutes, more preferably has a duration from about 45 minutes to about 75 minutes, and most preferably has a duration of about 60 minutes.

The conjugate-dNTPs of treatment 32 are preferably digoxigenin-dNTP conjugates. It is predicted that other conjugate-dNTPs, e.g. other plant steroid- or exogenous molecule-conjugates may perform satisfactorily as conjugate-dNTPs. Somewhat similarly, the nucleotide of the conjugate-dNTP may be any nucleotide, e.g. adenine, guanine, thymine, cytosine, uracil, or combinations thereof. Applicants, however, prefer to use a conjugate-dUTP.

Conjugate-dNTPs are added to tissue samples to provide a biologically effective amount. Similarly, TdT is added to tissue samples to provide a biologically effective amount. Biologically effective amounts are any amounts added by a stainer that successfully incorporate conjugate-dNTP into 3'-hydroxyl group ends of DNA cleaved as a result of apoptosis. Preferably, a biologically effective amount is achieved using any mix of conjugate-dNTPs and TdT that incorporates conjugate-dNTPs into 3'-hydroxyl group ends successfully by stainer and that allows for detection of apoptosis. For example, a biologically effective amount of conjugate-dNTPs and TdT made using components of the APOPTAG Detection Kit S7100 would comprise 33 parts TdT enzyme to 77 parts of reaction buffer containing conjugate-dNTPs. Other kit components designed for manual detection of apoptosis may be manipulated similarly to achieve applicant's unexpected results. If, however, conjugate-dNTPs and TdT are added to tissue samples separately, e.g., conjugate-nucleotides followed by TdT, similar ratios may be used.

Preferably, conjugate-dNTPs and TdT are added to said tissue as a mix having a volume between about 100 µl and about 600 µl, for example, about 200 µl, 300 µl, 400 µl or 500 µl, or any increments included there in. Most preferably, the mix is administered in about a 300 µl volume.

Primary stainer 2 performs rinse 34. Rinse 34 includes two TBS-tween rinse and blow treatments.

Primary stainer 2 performs stop buffer treatment 36. Preferably treatment 36 has a duration of about 5 minutes to about 15 minutes, and more preferably has a duration of about 10 minutes. Any amount of stop buffer sufficient to essentially terminate TdT activity is sufficient. Stop Buffer made for the present invention using components from APOPTAG Detection Kit S7100 is, preferably, about 1 part stock start buffer to about 34 parts water.

Primary stainer 2 performs anti-conjugate antibody treatment 42. Preferably, the anti-conjugate antibody reporter is an anti-digoxigenin antibody reporter. Others, however, using other conjugate-dNTPs may prefer to use antibodies specific to that conjugate, all variations of which would be within the scope of the present invention.

The reporter of the anti-conjugate antibody reporter may be selected from a variety of reporter molecules, e.g. fluorescent, radioactive or colorimetric. Preferably the reporter is colorimetric, and more preferably, the reporter is a peroxidase reporter capable of reporting in the presence of a chromogenic substrate.

Anti-conjugate antibody reporters, e.g., anti-digoxigenin antibody reporter, are added to tissue samples in a biologically effective amount. A biologically effective amount is any amount added by a stainer that allows for successful detection of apoptosis. For example, a biologically effective amount of anti-digoxigenin antibody reporter made using DAKO P5140 is 3.33 parts of anti-digoxigenin antibody peroxidase to 9996.67 parts antibody diluent.

Preferably, anti-digoxigenin antibody reporter is added to each sample as a solution having a volume between about 100 µl and about 600 µl. More preferably, it is added as a solution having a volume of about 300 µl. For example, it may be loaded into a stainer's reagent reservoir in an amount to provide a biologically effective concentration of anti-conjugate antibody reporter in about 100 µl to about 600 µl of solution, and more preferably, it is loaded to provide about 300 µl of solution per sample.

The duration of treatment 42 is preferably in between about 25 and about 50 minutes. The duration of treatment 42 may further depend on the type of tissue sample being analyzed. For example, with rat samples, the duration of treatment 42 is preferably in between about 25 and 35 minutes, and more preferably is about 30 minutes. For mice, primate, and human samples, the duration of treatment 42 is preferably in between about 40 and 50 minutes, and is more preferably about 45 minutes.

Primary stainer 2 performs rinse 44. Rinse 44 includes two TBS-tween rinse and blow treatments.

Primary stainer 2 performs reporter substrate treatment 46. Reporter substrate treatment 46 is preferably a peroxidase substrate and is even more preferably diaminobenzidine (DAB) (DAKO K3466, 1 drop per 1000 µl Tris Buffer). Other reporter substrates, e.g., 3-amino-9-ethylcarbazole (AEC), 4-chloro-1-napthol (CN), and p-phenylenediamine dihydrochloride/pyrocatechol (Hanker-Yates reagent), may be suitable and may be preferred by others. Additionally, others, using other reporters, e.g. non-enzymatic reporters, may choose not to use treatment 46. All of the above variations are within the scope of the present invention.

Primary stainer 2 performs rinse 50. Rinse 50 includes two $DH_2O$ treatments.

After treatment 50, samples are unloaded from primary stainer 2 and loaded into secondary stainer 4 for counterstaining 52. Counterstaining is preferably achieved using Gill's Hematoxylin (1 part stain to 3 parts water). Other suitable counterstains include Mayer's hematoxylin, eosin, and methyl green. While counterstaining 52, as illustrated, is performed by secondary stainer 4, performing counterstaining with primary stainer or another stainer is within the scope of the present invention.

Samples are evaluated 54 for the presence of reporting. Reporting may be any variety of qualitative or quantitative detection methods, and may be, for example, achieved through fluorescent, radioactive, or enzymatic activity. Preferably, evaluating for the presence of reporting includes evaluating for the presence of peroxidase-generated stain. The presence of the stain will preferably be detected through light microscopy, yet in some embodiments, evaluation may include visual inspection, e.g., unaided my microscopy; photospectometry; or image analysis.

The present invention also allows practitioners to eliminate steps previously required by traditional TUNEL assays, e.g., incubating slides in a specifically designed incubation chamber.

The utility and efficacy of the invention is set forth in the following example.

EXAMPLE

The following example, using various tissue samples, illustrates protocols by which methods of the invention can be successfully achieved. Tissue samples included human breast and prostate samples; rat, mouse, and primate brain samples; and human, rat, mouse, and primate colon samples. Samples were fixed, embedded in paraffin, and mounted on slides. Prior to performing the automated TUNEL assay, slides were deparaffinized as follows:

Deparaffinizing

A. Equipment and Supplies
1. Leica Automated H&E Stainer
2. Xylene
3. Ethanol—95% and 100%
4. DH$_2$O
5. Staining Dishes
6. Slide Racks
7. TBS Buffer w/tween (Signet Laboratories 2044)

B. Deparaffinize

Lids were removed from top row of reagents on Leica Automated H&E Stainer, and reagents were added. Slides were placed in the slide rack and loaded. Samples were deparaffinized using the following protocol:

| | |
|---|---|
| 1. Xylene | 5 minutes |
| 2. Xylene | 5 minutes |
| 3. Xylene | 5 minutes |
| 4. 100% Ethanol | 20 seconds |
| 5. 100% Ethanol | 20 seconds |
| 6. 95% Ethanol | 20 seconds |
| 7. 95% Ethanol | 20 seconds |
| 8. Tap H$_2$O | 20 seconds |
| 9. Tap H$_2$O | 20 seconds |
| 10. Tap H$_2$O | 20 seconds |

Slides were unloaded from the Leica Automated stainer and placed in DH$_2$O until loading onto the DAKO Autostainer. Slides that were not stained until the following day were placed in TBS buffer w/tween and stored at 4° C. overnight. Prior to staining, slides were allowed to reach room temperature.

Positive and negative control slides were run with each batch of slides for the automated TUNEL assay. Colon Cancer, or another positive cancer tissue, was used as the positive control.

Automated Assay

A. Equipment and Supplies
1. DAKO Automated Stainer
2. Adjustable microliter pipettes
3. Refrigerator
4. Vortex
5. Pipette tips
6. Lab towels
7. Transfer pipets
8. Antibody Diluent (DAKO S0809)
9. TBS Buffer w/tween (Signet Laboratories 2044)
10. Cardboard slide trays B. Premade Solutions
1. ApopTag Peroxidase In Situ Apoptosis Detection Kit (Serologicals Corporation S7100) (Chemicon)
   a. Proteinase K (DAKO S3020)
   b. H$_2$O$_2$ (VWR VW3540-2)
   c. Equilibration Buffer (#01, Component of the ApopTag Detection Kit S7100)
   d. Anti-Dioxigenin-Peroxidase (#05 Component of the ApopTag Detection Kit S7100) *Additional reagent not available separate from the ApopTag kit, therefore, DAKO Dioxigenin-peroxidase is used to maximize the number of slides that can be stained per kit.

C. Stock Solutions

| TdT (Components of the ApopTag Detection Kit S7100) | |
|---|---|
| TdT Enzyme (#03) | 33 μl |
| Reaction Buffer (#02) | 77 μl |

Enzyme and reaction buffer, containing dNTPs conjugates, were mixed and prepared fresh for each assay. Components were stored at −19° C. until ready to use.

| DAB (Diaminobenzidine) 2-component (DAKO K3466) | |
|---|---|
| Tris Buffer | 1000 μl |
| DAB | 1 drop |

DAB was made fresh before each use. Prior to use, DAB was mixed well and allowed to sit for 5 minutes.

| Anti-Dioxigenin 1:300 (DAKO P5104) | |
|---|---|
| Anti-Digoxigenin Antibody Peroxidase | 3.33 μl |
| Antibody Diluent | 996.67 μl |

Stock anti-dioxigenin antibody reporter was stored at 4° C. until ready for use and allow to reach room temperature before placing in stainer.

| Stop Buffer (Component of the ApopTag Detection Kit S7100) | |
|---|---|
| Stop Buffer (#04) | 1 ml |
| DH$_2$O | 34 ml |

Stop Buffer was mixed and stored at 4° C. until use.

| TBS Buffer w/tween (Signet Laboratories 2044) | |
|---|---|
| TBS Buffer w/tween | One 50 ml Stock Buffer |
| DH$_2$O | 950 Liters |
| Tween 20 | 2.5 milliliters |

Buffer pH was adjusted to 7.0 before use.

D. Automated Staining Protocol

Prior to assaying, the temperature of the room was measured and adjusted to about 24° C. and the humidity of the room was measured and adjusted to about 80%. Failure to adjust temperature and humidity adversely affected the results of staining.

The following protocol was developed and performed on the automated stainer (DAKO) for mouse, primate and human tissue samples:

| | |
|---|---|
| 1. TBS Buffer Rinse | |
| 2. Proteinase K | 30 minutes |
| 3. TBS Buffer Rinse and Blow | |

-continued

| | |
|---|---|
| 4. TBS Buffer Rinse and Blow | |
| 5. H$_2$O$_2$ | 5 minutes |
| 6. TBS Buffer Rinse and Blow | |
| 7. Equilibration Buffer | 10 minutes |
| 8. TBS Buffet Rinse and Blow | |
| 9. TBS Buffer Rinse and Blow | |
| 10. TdT Enzyme & dNTPs | 60 minutes |
| 11. TBS Buffer Rinse and Blow | |
| 12. TBS Buffer Rinse and Blow | |
| 13. Stop Buffer | 10 minutes |
| 14. TBS Buffer Rinse and Blow | |
| 15. TBS Buffer Rinse and Blow | |
| 16. Anti-Digoxigenin Antibody Reporter | 45 minutes |
| 17. TBS Buffer Rinse and Blow | |
| 18. TBS Buffer Rinse and Blow | |
| 19. DAB | 5 minutes |
| 20. DH$_2$O Rinse | |
| 21. DH$_2$O Rinse | |

Slides were removed after the completion of running and placed in DH$_2$O.

The following protocol was developed and performed on the automated stainer (DAKO) for rat samples:

| | |
|---|---|
| 1. TBS Buffer Rinse | |
| 2. Proteinase K | 60 minutes |
| 3. TBS Buffer Rinse and Blow | |
| 4. TBS Buffer Rinse and Blow | |
| 5. H$_2$O$_2$ | 5 minutes |
| 6. TBS Buffer Rinse and Blow | |
| 7. Equilibration Buffer | 10 minutes |
| 8. TBS Buffer Rinse and Blow | |
| 9. TBS Buffer Rinse and Blow | |
| 10. TdT Enzyme & dNTPs | 60 minutes |
| 11. TBS Buffer Rinse and Blow | |
| 12. TBS Buffer Rinse and Blow | |
| 13. Stop Buffer | 10 minutes |
| 14. TBS Buffer Rinse and Blow | |
| 15. TBS Buffer Rinse and Blow | |
| 16. Anti-Digoxigenin Antibody | 30 minutes |
| 17. TBS Buffer Rinse and Blow | |
| 18. TBS Buffer Rinse and Blow | |
| 19. DAB | 5 minutes |
| 20. DH$_2$O Rinse | |
| 21. DH$_2$O Rinse | |

Slides were removed after the completion of running and placed in DH$_2$O. The remaining protocol is similar for mouse, primate, human and rat.

IV. Clearing and Coverslipping

A. Equipment and Supplies
1. Leica H&E Stainer
2. Leica Coverslipper
3. Ethanol—95% and 100%
4. Xylene
5. Hematoxylin
6. Mounting medium
7. Coverslips
8. Staining racks
9. Slide racks
10. Slide trays
11. Lab towels
12. Tap H$_2$O
13. DH$_2$O B. Counterstaining
1. Slides were removed from the DAKO staining racks and loaded into slide racks on the Leica H&E stainer. Slides were treated with the following protocol:

| | |
|---|---|
| 1. H$_2$O | 20 seconds |
| 2. Gill's Hematoxylin* | 1 minute 30 seconds |
| 3. H$_2$O | 1 minutes |
| 4. Bluing | 1 minute |
| 5. H$_2$O | 5 minutes |
| 6. 95% ethanol | 1 minute |
| 7. 95% ethanol | 20 seconds |
| 8. 100% ethanol | 20 seconds |
| 9. 100% ethanol | 20 seconds |
| 10. 100% ethanol | 30 seconds |
| 11. Xylene | 30 seconds |
| 12. Xylene | 1 minute |
| 13. Xylene | 1 minute |

*Gill's Hematoxylin Working Solution (Fisher #CS400-10)
1 part Gill's
3 parts DH$_2$O
2. After counterstaining slides were transferred to a coverslipper (Leica).

Results

The above protocol for mouse, primate, and human produced successful apoptosis detection in all mouse, primate and human samples based on comparison to positive and negative controls. Brown to a blackish-brown staining in the nuclei, including darker brown to black rods within the nuclei, was indicative of apoptosis. Background was clear to light beige and complimented by a very light bluish-purple.

The above protocol for rat produced successful apoptosis detection in rats. The presence of apoptosis was determined as above.

Other protocols had numerous problems. For example, other protocols failed to show apoptosis on positive controls; produced high background; produced nonspecific staining; or had positive results masked by counterstain.

Numerous characteristics and advantages have been set forth in the foregoing description, together with details of structure and function. The novel features are pointed out in the appended claims. The disclosure, however, is illustrative only, and changes may be made in detail, especially in matters of shape, size, and arrangement of parts, within the principle of the invention, to the full extent indicated by the broad general meaning of the terms in which the general claims are expressed.

I claim:
1. A TUNEL assay method comprising:
adjusting the relative humidity of the room in which said assay is to be performed to about 80%;
adjusting the temperature of the room in which said assay is to be performed to about 22° C. to about 26° C.;
loading slides having mounted tissue samples into an immunochemical stainer; and
testing said tissue samples for apoptosis using at least said immunochemical stainer or another histological stainer wherein said testing comprises
adding conjugate-dNTPs to said tissue with said immunochemical stainer or said histological stainer,
adding TdT to said tissue with said immunochemical stainer or said histological stainer;
rinsing said tissue with TBS-tween; and
adding anti-conjugate antibody reporter with said immunochemical stainer or said histological stainer.

2. The assay method of claim 1, wherein said temperature adjusting to about 24° C.

3. The method of claim 1, wherein said conjugate-dNTPs are digoxigenin-dNTP conjugates.

4. The method of claim 3, wherein said digoxigenin-dNTP conjugates are added to said tissue as a biologically effective amount.

5. The method of claim 1, wherein said TdT is added to said tissue as a biologically effective amount.

6. The method of claim 1, wherein said conjugate-dNTPs and said TdT are added to said tissue as a mix having a volume between about 100 μl and about 600 μl.

7. The method of claim 1, wherein said anti-conjugate antibody reporter is an anti-digoxigenin antibody reporter added to said tissue in a biologically effective amount.

8. The method of claim 7, wherein said anti-digoxigenin antibody reporter is added as a solution having a volume between about 100 μl and about 600 μl.

9. The method of claim 1, wherein said anti-conjugate antibody reporter includes a reporter selected from the group consisting of fluorescent, radioactive and colorimetric reporters.

10. The method of claim 1, wherein said anti-conjugate antibody reporter includes a peroxidase reporter capable of reporting in the presence of a chromogenic substrate.

11. The method of claim 1, wherein said anti-conjugate antibody reporter is added for a duration of between about 25 and about 50 minutes.

12. The method of claim 11, wherein said anti-conjugate antibody reporter duration is between about 25 and 35 minutes for rat samples.

13. The method of claim 12, wherein said anti-conjugate antibody reporter duration is about 30 minutes for rat samples.

14. The method of claim 11, wherein said anti-conjugate antibody reporter duration is between about 40 and 50 minutes for mice, primate, and human samples.

15. The method of claim 14, wherein said anti-conjugate antibody reporter duration is about 45 minutes for mice, primate, and human samples.

16. The method of claim 1, further including evaluating for the presence of reporting.

17. The method of claim 16, wherein said evaluating for the presence of reporting includes evaluating for peroxidase-generated stain.

18. The method of claim 1, further including adding proteinase prior to said testing.

19. The method of claim 18, wherein said adding proteinase includes adding between about 100 μl and about 600 μl of Proteinase K to said tissue for a duration.

20. The method of claim 19, wherein said Proteinase K duration is between about 20 minutes and about 70 minutes.

21. The method of claim 20, wherein said Proteinase K duration is between about 20 minutes and about 40 minutes for mice, primate, and human samples.

22. The method of claim 21, wherein said Proteinase K duration is about 30 minutes for mice, primate, and human samples.

23. The method of claim 20, wherein said Proteinase K duration is between about 50 and about 70 minutes for rat samples.

24. The method of claim 23, wherein said Proteinase K duration is about 60 minutes for rat samples.

25. The method of claim 1, further including deparaffinizing said slides prior to said testing with a stainer.

26. The method of claim 25, wherein said deparaffinizing is achieved automatically by said primary stainer.

27. The method of claim 1, wherein said testing further includes adding a reporter substrate.

28. A TUNEL assay method using a stainer having a plurality of reservoirs, said assay comprising:
    loading a reagent reservoir of a primary stainer with anti-conjugate antibody reporter;
    loading a slide tray of said primary stainer with a slide having a tissue sample; and
    adding said anti-conjugate antibody reporter to said sample for a duration with said primary stainer and further including loading a TdT and conjugate-dNTP mix into another of said reservoirs, and adding said TdT and conjugate mix to said tissue with said stainer prior to the addition of said anti-conjugate antibody reporter for a duration; and rinsing said tissue with TBS-tween prior to the addition of said anti-conjugate antibody report for a duration.

29. The method of claim 28, wherein said anti-conjugate antibody reporter is an anti-digoxigenin antibody reporter.

30. The method of claim 28, wherein said anti-conjugate antibody reporter is loaded into said reagent reservoir in an amount to provide about 100 μl to about 600 μl of biologically effective anti-conjugate antibody reporter per sample.

31. The method of claim 30, wherein said anti-conjugate antibody reporter is loaded to provide about 300 μl of solution per sample.

32. The method of claim 28, wherein said anti-conjugate antibody reporter duration is between about 20 minutes and about 50 minutes.

33. The method of claim 32, wherein said anti-conjugate antibody reporter duration is in between about 40 minutes and about 50 minutes for mice, primate, and human samples.

34. The method of claim 33, wherein said anti-conjugate antibody reporter duration is about 45 minutes for mice, primate, and human samples.

35. The method of claim 32, wherein said anti-conjugate antibody reporter duration is between about 20 minutes and about 40 minutes for rat samples.

36. The method of claim 35, wherein said anti-conjugate antibody reporter duration is about 30 minutes for rat samples.

37. The method of claim 28, wherein said conjugate-dNTP includes a digoxigenin-dNTP.

38. The method of claim 37, wherein said digoxigenin-dNTP includes a digoxigenin-dUTP.

39. The method of claim 28, wherein said mix is loaded to provide a biologically effective amount of TdT to said tissue.

40. The method of claim 39, wherein said mix amount is administered in a volume between about 100 μl to about 600 μl per sample.

41. The method of claim 28, wherein said TdT and conjugate dNTP mix duration is about 60 minutes.

42. The method of claim 28, further including loading a proteinase into another of said reservoirs, and
    adding said proteinase to said tissue with said stainer prior to the addition of said anti-conjugate antibody reporter for a duration.

43. The method of claim 42, wherein said proteinase includes Proteinase K.

44. The method of claim 43, wherein said Proteinase K is loaded to provide about 100 μl to about 600 μl per sample.

45. The method of claim 42, wherein said proteinase duration is from about 20 minutes to about 70 minutes.

46. The method of claim 45, wherein said proteinase duration is from about 20 minutes to about 40 minutes for mouse, primate, and human samples.

47. The method of claim 46, wherein said proteinase duration is about 30 minutes for mouse, primate and human samples.

48. The method of claim 47, wherein said proteinase duration is from about 50 minutes to about 70 minutes for rat samples.

49. The method of claim 48, wherein said proteinase duration is about 60 minutes for rat samples.

50. The method of claim 28, further including adding a reporter substrate after the addition of said anti-conjugate antibody reporter.

51. A TUNEL assay method comprising:

adjusting the relative humidity of the room in which said assay is to be performed to about 80%;

adjusting the temperature of the room in which said assay is to be performed to about 22° C. to about 26° C.;

loading an immunochemical stainer with reagents for applying to tissue samples, said reagents including buffer, Proteinase K, conjugate-dNTPs, TdT, and, anti-conjugate antibody reporter;

deparaffinizing said samples;

adding Proteinase K to said tissue sample for a duration with said immunochemical stainer;

adding conjugate-dNTPs to said tissue sample for a duration with said immunochemical stainer;

adding TdT to said tissue sample for a duration with said immunochemical stainer; rinsing said tissue with TBS-tween; and adding anti-conjugate antibody reporter to said tissue sample for a duration with said immunochemical stainer.

* * * * *